United States Patent [19]

Anand et al.

[11] Patent Number: 4,818,254

[45] Date of Patent: Apr. 4, 1989

[54] SEMI-PERMEABLE MEMBRANES CONSISTING PREDOMINANTLY OF POLYCARBONATES DERIVED FROM TETRAHALOBISPHENOLS

[75] Inventors: Joginder N. Anand, Clayton; Darrell C. Feay, Orinda, both of Calif.; Stephen E. Bales, Midland, Mich.; Thomas O. Jeanes, Antioch, Calif.

[73] Assignee: The Dow Chemical Company, Midland, Mich.

[21] Appl. No.: 141,878

[22] Filed: Jan. 6, 1988

Related U.S. Application Data

[63] Continuation-in-part of Ser. No. 851,758, Apr. 14, 1986, abandoned.

[51] Int. Cl.⁴ .............................................. B01D 53/22
[52] U.S. Cl. ......................................... 55/316; 55/68; 55/158; 528/202
[58] Field of Search .......................... 55/16, 68, 158; 528/196, 202

[56] References Cited

U.S. PATENT DOCUMENTS

| | | | |
|---|---|---|---|
| 3,038,874 | 6/1962 | Laakso et al. | 528/202 X |
| 3,038,879 | 6/1962 | Laakso et al. | 528/202 X |
| 3,119,787 | 1/1964 | Laasko et al. | 528/202 |
| 3,128,264 | 4/1964 | Laaksо et al. | 528/202 X |
| 3,256,675 | 6/1966 | Robb | 55/16 |
| 3,615,024 | 10/1971 | Michaels | 210/490 |
| 3,876,580 | 4/1975 | Nouvertne et al. | 528/202 X |
| 3,890,266 | 6/1975 | Serini et al. | |
| 3,912,687 | 10/1975 | Haupt et al. | 528/202 X |
| 3,945,926 | 3/1976 | Kesting | 264/41 X |
| 4,032,309 | 6/1977 | Salemme | 55/158 |
| 4,075,108 | 2/1978 | Higley et al. | 264/41 X |
| 4,086,310 | 4/1978 | Bottenbruch et al. | 55/158 X |
| 4,170,587 | 10/1979 | Schmidt et al. | 528/202 X |
| 4,281,101 | 7/1981 | Schreckenberg et al. | 528/202 X |
| 4,297,455 | 10/1981 | Lindner et al. | 528/202 X |
| 4,374,891 | 2/1983 | Ward, III | 428/220 |
| 4,377,662 | 3/1983 | Loucks | 528/202 X |

FOREIGN PATENT DOCUMENTS

| | | | |
|---|---|---|---|
| 99187 | 1/1984 | European Pat. Off. | 55/158 |
| 53-16373 | 2/1978 | Japan . | |
| 66880 | 6/1978 | Japan | 55/16 |
| 8506 | 1/1983 | Japan | 55/158 |
| 8511 | 1/1983 | Japan | 55/158 |
| 56107351 | 1/1983 | Japan . | |
| 58-223411A | 12/1983 | Japan . | |
| 59-22724 | 2/1984 | Japan . | |
| 120206 | 7/1984 | Japan | 55/158 |
| 177120 | 10/1984 | Japan | 55/16 |
| 857430 | 12/1960 | United Kingdom | 528/202 |
| 2011804A | 7/1979 | United Kingdom . | |

OTHER PUBLICATIONS

Muruganandam, University of Texas at Austin, Separations Research Program, paper presented at fall meeting on Oct. 28 and 29, 1985, "Absorption and Transport in Substituted Polycarbonates and Polystyrene/Tetramethyl Polycarbonate Blends".

Chern et al., Chapter 2 "Material Selection for Membrane Based Gas Separations", *Material Science of Synthetic Membranes*, Lloyd, Ed., pp. 25–46, American Chemical Society (1985).

*Primary Examiner*—Robert Spitzer
*Attorney, Agent, or Firm*—Norman L. Sims

[57] ABSTRACT

The invention is an improved gas separation membrane comprising a thin, discriminating layer consisting predominantly of a carbonate polymer derived from a bisphenol corresponding to Formula I

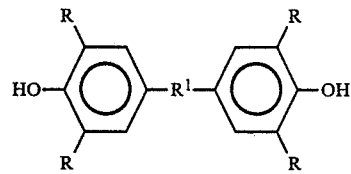

wherein R at each occurrence is independently H, Cl, Br, or $C_1$–$C_4$ alkyl and $R^1$ is

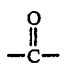

—S—, —SO$_2$—, —O—, or a $C_1$–$C_6$ divalent hydrocarbon or a $C_1$–$C_6$ divalent fluorocarbon radical or inertly substituted hydrocarbon radical, with the proviso that at least 25 weight percent of the moieties derived from the bisphenol of Formula I present in the discriminating layer bear R groups which are exclusively Br or Cl, the gas separation membrane exhibiting a separation factor for oxygen and nitrogen at 24° C. of at least 6.1. In another aspect this invention relates to a process for separating oxygen from nitrogen, or a nitrogen-containing gas.

59 Claims, No Drawings

SEMI-PERMEABLE MEMBRANES CONSISTING PREDOMINANTLY OF POLYCARBONATES DERIVED FROM TETRAHALOBISPHENOLS

CROSS-REFERENCE TO RELATED APPLICATION

This application is a continuation-in-part of Serial No. 851,758, filed Apr. 14, 1986, now abandoned.

BACKGROUND OF THE INVENTION

This invention relates to semi-permeable membranes derived from polycarbonates wherein the polycarbonates are derived in a significant portion from tetrahalobisphenols. The invention further relates to the use of these membranes to separate certain gases, for example, oxygen from nitrogen, and carbon dioxide from methane.

In various industries, it is necessary or highly desirable to separate one component from another in a gaseous stream. Processes used to perform such separations include pressure swing adsorption and membrane separations. In a membrane separation, a gaseous stream containing the components to be separated is contacted with a membrane, wherein the membrane separates two regions in a manner such that only those materials which permeate through the membrane can communicate from one region to the other. Such membranes are semi-permeable, in that one component of the gaseous mixture selectively permeates through the membrane at a rate much higher than one or more of the components in the gaseous stream. The gaseous mixture is contacted with the membrane in a manner such that the selectively permeable species is preferentially transported through the membrane to the other region. It is to be noted that the component from which the selectively permeable species is to be separated may in fact permeate through the membrane at a much slower rate than the selectively permeable species. It is this difference in rates of permeation which is used to separate the gaseous species or reduce the concentration of the less selectively permeated species in the region to which the permeating gases permeate.

In such separations, the relative rate of permeation, that is, the difference in rate of permeation between the selectively permeating gas and the non-selectively permeating gas, is a major factor in the separation achieved. The higher the ratio of permeation of the selectively permeable gas over the non-selectively permeable gas, the better the membrane will perform. Therefore, it is desirable to have as high a ratio as possible.

Presently, membranes derived from acetate esters, for example cellulose triacetate, and olefins, for example polyethylene, polypropylene, poly-4-methylpentene-1, are used for gas separations. Among such separations are the separation of oxygen from nitrogen, and carbon dioxide from methane.

Some of the materials used in membranes suffer from certain disadvantages. One such problem is the inability to perform under extreme conditions, such as high temperatures and pressures. As a result, certain separations are limited by the membrane as to the temperatures and pressures which may be used.

What are needed are membranes with a high relative rate of permeation through the membrane of the selectively permeating species over the non-selectively permeating species. Further, what is needed is a membrane which has enhanced mechanical strength so as to withstand more extreme temperatures and pressures.

SUMMARY OF THE INVENTION

The invention is an improved gas separation membrane comprising a thin discriminating layer comprising a polycarbonate polymer derived from a bisphenol corresponding to formula I

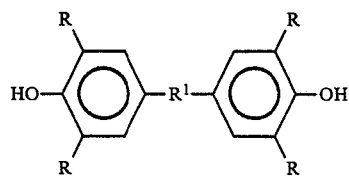

Formula I where R at each occurrence is independently H, Cl, Br, or $C_1$–$C_4$ alkyl and $R^1$ is

—S—, —SO$_2$—, —O—, or a $C_1$–$C_6$ divalent hydrocarbon or a $C_1$–$C_6$ divalent fluorocarbon radical or inertly substituted $C_{1-6}$ divalent hydrocarbon radical, with the proviso that at least 25 weight percent of the moieties derived from the bisphenol of formula I present in the discriminating layer bear R groups which are exclusively Br, Cl, or mixtures thereof, said gas separation membrane exhibiting a separation factor for oxygen and nitrogen at 24° C. of at least 6.1.

In another aspect, this invention relates to a process for separating oxygen from nitrogen, or a nitrogen-containing gas.

The membranes of this invention demonstrate surprisingly high separation factors for oxygen and nitrogen separations. Further, the membranes of this invention demonstrate surprisingly high separation factors for the separation of carbon dioxide from methane. The membranes of this invention have good mechanical properties and therefore are useful under more extreme conditions, for example temperature and pressure.

DETAILED DESCRIPTION OF THE INVENTION

The membranes of this invention are prepared from polycarbonates derived from bisphenols wherein a significant portion of the bisphenols used to prepare the polycarbonates are tetrahalo-substituted, more particularly the tetrahalo substituents are found in the 3,5-positions on the aromatic or phenolic rings. The presence of a significant portion of the residue of tetrahalo bisphenols enhance the membrane properties of membranes that are prepared therefrom. More particularly, such membranes have enhanced separation factors with respect to oxygen/nitrogen separations and carbon dioxide/methane separations.

Preferably, at least 35 weight percent of the moieties derived from the bisphenol of formula I present in the discriminating layer bear R groups which are exclusively bromine, chlorine, or mixtures thereof. More preferably, at least 50 weight percent of the moieties derived from the bisphenol of formula I present in the discriminating layer bear R groups which are exclusively bromine, chlorine, or mixtures thereof. Even more preferably, at least 75 weight percent of the moieties derived from the bisphenol of formula I present in the discriminating layer bear R groups which are exclusively bromine, chlorine, or mixtures thereof. Even more preferably, the polycarbonate is derived from bisphenols of formula I, where R is exclusively bromine, chlorine, or mixtures thereof. In the embodiment wherein the polycarbonate is prepared from tetrachlorobisphenols, it is preferable that the polycarbonate backbone contain about 90 percent by weight or greater units derived from tetrachloro bisphenols, more preferably 95 percent by weight, and most preferably 100 percent by weight. Bromine is the preferred halogen herein. Examples of preferred bisphenols of formula I which bear R groups which are exclusively Br or Cl are 2,2-bis-(3,5-bromo-4-hydroxyphenyl)propane and 2,2-bis(3,5-chloro-4-hydroxyphenyl)propane with 2,2-bis(3,5-bromo-4-hydroxyphenyl)propane being most preferred.

phenol of Formula IV, even more preferably between about 0 and 50% of a bisphenol of Formula IV, and 50 and 100% of a bisphenol of Formula III. Even more preferably, polycarbonate is derived from between about 75% and 100 of a bisphenol corresponding to Formula III, and between about 0 and 25% of a bisphenol corresponding to Formula IV.

In a most preferred embodiment, the polycarbonate is derived exclusively from bisphenols corresponding to Formula III. Examples of bisphenols within the scope of Formula IV include 2,2-bis(4-hydroxyphenyl)-propane, 2,2-bis(3,5-methyl-4-hydroxyphenyl)propane, and the like.

The polymers prepared from bisphenols of Formula III and Formula IV preferably have recurring units which correspond to the formula

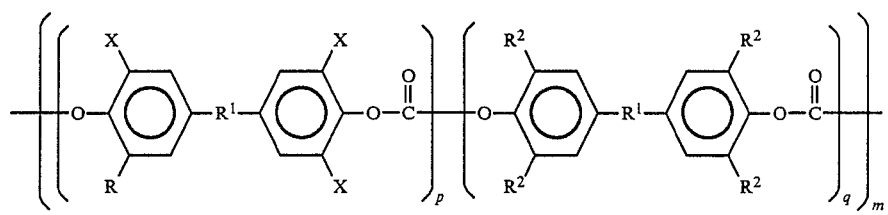

The polycarbonates used in this invention preferably correspond to the following formula

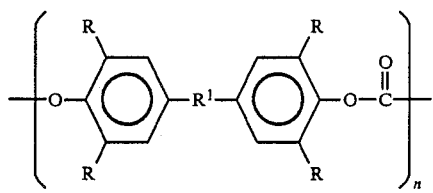

wherein R and $R^1$ are as hereinbefore defined and n is an integer of about 50 or greater. Preferably, the polycarbonates of this invention are derived from between about 25 and 100% of a bisphenol corresponding to the formula

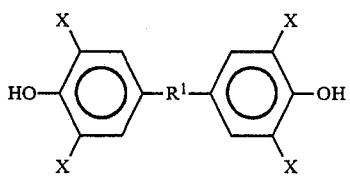

Formula III and between about 0 and 75% of a bisphenol corresponding to the following formula

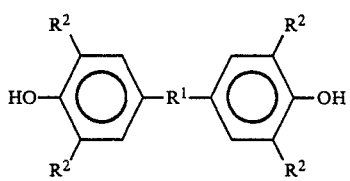

Formula IV wherein $R^1$ is as hereinbefore defined, $R^2$ is hydrogen or $C_1$-$C_4$ alkyl, and X is independently in each occurrence chlorine or bromine. Preferably the polycarbonate is derived from between about 35 and 100% of a bisphenol of Formula III and between about 0 and 65% of a biswherein $R^1$, $R^2$ and X are as hereinbefore defined, p is a number of between about 15 and 100, q is a number of between about 0 and 85, and m is a positive real number, such that the polymer the formula represents has sufficient molecular weight to prepare a membrane with suitable characteristics.

In the embodiment wherein the polycarbonate of this invention is derived from bisphenols which correspond both to Formula III and to Formula IV, $R^2$ is preferably $C_{1-4}$ alkyl, and most preferably methyl. In a more preferred embodiment the polycarbonate used to prepare membranes in this invention is a copolymer of 2,2-bis(3,5-dibromo-4-hydroxyphenyl)propane and 2,2'-bis-(3,5-dimethyl-4-hydroxyphenyl)propane.

In the hereinbefore presented formulas, R is preferably chlorine, bromine or $C_{1-4}$ alkyl, more preferably chlorine, bromine or methyl, even more preferably chlorine and bromine, and most preferably bromine. $R^1$ is preferably a $C_{1-6}$ divalent hydrocarbon, more preferably a $C_{1-6}$ alkylidene radical, even more preferably a propylidene radical. The polycarbonates of this invention can be prepared by any process known in the art which prepares polycarbonates with suitable properties for membrane formation. See *Encyclopedia of Polymer Science & Technology*, Editor Mark et al, Interscience Division of John Wiley & Sons, N.Y., N.Y., 1969, Vol. 10, pp. 714–725 (relevant portions incorporated herein be reference). The polymers of this invention should be polymerized to the extent that the polymers will form a membrane with sufficient mechanical strength to withstand use conditions. Preferably, the polymer has an inherent viscosity of 0.35 or greater and more preferably 0.40 or greater, and preferably has a molecular weight of 60,000 or greater.

The novel membranes of this invention can take any form known to one skilled in the art. In particular, the membrane may be a homogeneous membrane, a composite membrane, or an asymmetric membrane. Furthermore, the membranes may be in the form of a flat sheet, a hollow tube, or a hollow fiber. One skilled in the art would readily know how to prepare a membrane in any of the aforementioned forms. As used herein, the term semi-permeable membrane refers to a membrane which displays different permeabilities for different species of molecules, and therefore, may be used in the separation of ions and molecules having different permeabilities across the membrane. Permeate as used herein refers to those species which permeate through the membrane at a much faster rate than other species. Non-permeate refers herein to those species which permeate at a much slower rate than the other species present.

Preferably, the membranes of this invention are asymmetric or composite membranes, and most preferably asymmetric membranes.

Homogeneous and composite membranes are prepared by forming a thin, discriminating layer which is dense and free of voids and pores. Such membranes or layers have generally the same structure and composition throughout the membrane. In one preferred embodiment, the polycarbonates of this invention are dissolved in a water-miscible solvent, for example dimethylformamide, N-methyl pyrrolidone, or dimethylacetamide. Preferably, the solution contains polymer in weight percents of between about 5 and 75, more preferably between about 10 and 40, and most preferably between about 15 and 20 percent. This solution should have sufficient viscosity to allow casting of the solution onto a flat surface. The solution should be homogeneous. Thereafter, the polymer is cast on a surface, and in the case of a homogeneous membrane on a surface from which the finished membrane may readily be separated. A convenient way of carrying out this operation is either by casting the membrane solution onto a support surface which may be dissolved away from the finished film following the drying and curing step or by casting the membrane onto a support having low surface energy, such as silicone, coated glass, or a surface to which the membrane will not adhere, such as mercury. Casting is done by pouring the solution onto the appropriate surface and sizing using the appropriate tool, to form a solution of the appropriate thickness. Thereafter, the cast solution is exposed to drying or curing conditions. Such conditions are used to remove the solvent thereby leaving a thin, discriminating layer of polymer which is homogeneous. The solution can be dried either by exposure to a vacuum, exposure to elevated temperatures, by allowing the solvent to evaporate by time, or any combination thereof. Generally, it is preferable to expose the cast solution to elevated temperatures, preferably less than about 100° C. In one preferred embodiment, such exposure is done in a vacuum oven or under vacuum conditions at elevated temperatures. Preferably, the homogeneous membrane has a thickness of between about 0.5 and 10.0 mils, and most preferably between about 1 and 3 mils.

To prepare a composite membrane, a homogeneous thin, discriminating layer can be formed, and thereafter adhered to a porous support after formation. Alternatively, the porous support can be the surface upon which the membrane is cast. In such embodiment, the composite membrane is prepared by casting a forming solution as a uniform coating on the porous support which forms the support layer for the finished membrane. Penetration of the polymer from which the thin, discriminating layer is formed into pores of the porous supporting layer and the layer itself is acceptable so long as the desired thickness of the semi-permeable membrane is not exceeded. In a composite membrane, the membrane is supported on a porous substrate or structure. This porous supporting layer is characterized in that it does not greatly impede the transport across this layer of all components of a fluid in contact with the porous layer. The porous supporting layer can comprise a discriminating layer which impedes the transportation of some fluid components to the discriminating layer, but generally this second discriminating layer is not necessary or desirable. In one embodiment, the supporting layer can be a metal or polymeric plate with a plurality of holes drilled through it. However, such a drill plate is not advantageous because it can significantly reduce the effective area of the membrane. In a preferred embodiment, the porous supporting layer is a very porous polymer membrane. Illustrative of such polymeric supporting layers are cellulose ester and microporous polysulfone membranes. Such membranes are commercially available under the trade names MILLIPORE, PELLICON and DIAFLOW. Where such supporting membranes are thin or highly deformable, a frame may also be necessary to adequately support the semi-permeable membrane. In one especially preferred embodiment, the polymeric supporting layer is a hollow fiber of microporous polymer such as polysulfone, cellulose acetate, or some other cellulose ester. The hollow fiber itself provides adequate support for the semi-permeable membrane layer coated on the inside or outside surface of the fiber. Polysulfone hollow fibers are most preferred for this application. After the solution useful in forming the thin, discriminating layer is cast on the porous support, the porous support and solution cast thereon are then exposed to conditions for removal of the solvent so as to form the dense skin. Such conditions are similar to those described hereinbefore for the formation of the homogeneous membrane.

To form an asymmetric membrane, a solution is cast as described hereinbefore, and thereafter the cast solution is partially cured to remove a portion of the solvent. Thereafter, one or both surfaces of the partially dried membrane is contacted with a water quench so as to form a thin, non-porous, discriminating layer on one or both sides of the membrane under conditions such that the solvent away from the dense layer communicates to the dense layer forming pores in the remainder of the membrane, thereby forming an asymmetric membrane. Such porous layer is present to provide support for the thin, discriminating layer without impeding the transport of the fluid containing the components to be separated by the semi-permeable, thin, discriminating layer. The partial curing step is performed in a manner similar to the curing step described with respect to the formation of homogeneous membranes.

Hollow fiber membranes can be formed by spinning fibers from an appropriate solution of the polycarbonate in a water-miscible solvent. Such spinning is well known to those skilled in the art, and the formation of hollow fibers which are homogeneous, asymmetric, or composite membranes, require the adaptation of the hereinbefore described procedures to the hollow fiber form of the membrane. Such adaptations are well within the skill of the art.

Generally, the thin, discriminating layer in a composite or asymmetric form of a membrane has a thickness of between about $0.05\mu$ and $10\mu$, more preferably between about $0.2\infty$ and $2\mu$.

In one preferred embodiment, the membranes are annealed before use. It is believed that annealing increases the separation factor for oxygen-nitrogen separations. The membrane is exposed to temperatures above the beta transition and below the glass transition temperature for a period of time to partially densify the polymer. This procedure can optionally be performed under vacuum. For tetrabromo bisphenol A, temperatures between 185° and 230° C. are preferred.

Under certain conditions, it may be highly desirable to provide support to the membrane when the membrane is employed in a separation apparatus or process. In one embodiment, the peripheral area of the membrane is affixed to a framing structure which supports the outer edge of the membrane. The membrane can be affixed to the framing structure by a clamping mechanism, adhesive, chemical bonding, or other techniques known in the prior art. The membrane affixed to the frame can then be sealingly engaged in the conventional manner in a vessel so that the membrane surface inside the framing support separates two otherwise non-communicating compartments in the vessel. The skilled artisan will recognize that the structure which supports the membrane can be an integral part of the vessel or even the outer edge of the membrane.

In one embodiment, this invention is a process for separating oxygen from nitrogen which comprises contacting a gaseous stream containing oxygen and nitrogen with the membrane of this invention under conditions such that oxygen selectively permeates through the membrane, in comparison to nitrogen. Preferably, the membrane is sealingly engaged to a vessel which defines a space communicating with only one side of the membrane, such that the permeable oxygen contacting the other side of the membrane can permeate through the membrane to the non-communicating space, at a significantly faster rate than the nitrogen communicates or permeates through the membrane. Preferably, the oxygen and nitrogen are a part of an air stream. Preferably, the pressure on the communicating side of the membrane is between about 40 psia (about 275 kPa) and about 200 psia (about 1379 kPa), more preferably between about 80 (about 552 kPa) and about 120 psia (about 827 kPa). The temperature at which the mixed oxygen and nitrogen stream is contacted with the membrane is between about 0° and 80° C., most preferably between about 5° and 45° C. The pressure differential across the membrane is preferably between about 40 psia (about 275 kPa) and about 200 psia (about 1379 kPa), and more preferably between about 95 (about 655 kPa) and about 120 psia (about 827 kPa). In one preferred embodiment, the membrane is in a hollow fiber form. Wherein the embodiment wherein the membrane is in hollow fiber form, it is preferable to contact the mixed nitrogen and oxygen stream with a membrane on the outside of the hollow fiber under conditions such that the oxygen selectively permeates into the hollow fibers and a stream which is rich in oxygen is taken off of the end of the hollow fiber. This oxygen enriched stream can be further oxygen enriched by contacting with one or more membranes in succession.

In a similar manner, the membranes of this invention can be used to separate carbon dioxide from methane.

In that embodiment wherein at least 35 weight percent of the moieties derived from Formula I present in the discriminating layer bear R groups which are exclusively bromine, the gas separation membrane exhibits a separation factor for oxygen over nitrogen of at least 6.4. In that embodiment wherein the discriminating layer is derived exclusively from bisphenols in which the R is exclusively Br, the separation factor is at least 7.0 at 20° C. In that embodiment wherein the discriminating layer is derived exclusively from bisphenols in which R is exclusively chlorine, the separation factor is preferably at least 6.2 at 20° C., and more preferably 6.4 at 20° C.

The membrane of this invention preferably has a reduced flux for oxygen of $3.35 \times 10^{-9}$ cc/cm$^2$-sec cmHg or greater, more preferably the membrane has a reduced flux for oxygen of $1.12 \times 10^{-8}$ cc/cm$^2$-sec cmHg or greater, and most preferably a reduced flux of $6.72 \times 10^{-8}$ cc/cm$^2$-sec cmHg or greater. In the embodiment wherein the membrane is asymmetric or a composite, the membrane preferably has a reduced flux for oxygen of $8.53 \times 10^{-8}$ cc/cm$^2$-sec cmHg, more preferably the membrane has a reduced flux for oxygen of $5.69 \times 10^{-6}$ (at 0.15 microns)$\times 10^{-5}$ or greater, and most preferably the membrane has a reduced flux for oxygen of $1.70 \times 10^{-5}$ (at 500Å) or greater. Preferably the membrane has a flux of $1.77 \times 10^{-5}$ cc/cm$^2$-sec or greater, more preferably the membrane has a flux of $1.18 \times 10^{-3}$ cc/cm$^2$-sec or greater, and most preferably the membrane has a flux of $3.52 \times 10^{-3}$ cc/cm$^2$-sec or greater.

In certain embodiments, the separations of oxygen from nitrogen occurs at lower temperatures, preferably at about 10° C. or below. It has been discovered that the membranes useful in this invention have surprisingly high separation factors at 10° C. or below. Such separation factors are preferably 8.0 or greater, more preferably 8.5 or greater, and even more preferably 9.0 or greater at 10° C. or below.

SPECIFIED EMBODIMENTS

The following examples are included for illustrative purposes only and do not limit the scope of the claims or the invention. Unless otherwise stated, all parts and percentages are by weight.

EXAMPLE 1

Membrane of 100% Tetrabromo Bisphenol A Polycarbonate

Polymerization Procedure

A three-neck, 1.0 liter round-bottom flask, equipped with a thermometer, air-driven stirrer and glass funnel, is charged with 500 cc of methylene chloride, 108.8 grams (0.2 moles) of 3,3',5,5' tetrabromo bisphenol A, 0.3 grams (0.002 moles) of p-tertiary butyl phenol and 42 cc (0.52 moles) of pyridine. The resultant clear, pale yellow solution is stirred under a nitrogen atmosphere for ten minutes. Moderate stirring is continued and 23.5 grams (0.238 moles) of phosgene are bubbled into the reaction over a forty-one minutes period.

The pale yellow, turbid solution is then scavenged with methanol, neutralized with dilute hydrochloric acid and washed a second time with dilute hydrochloric acid. The slightly opaque solution is clarified by passing it through an MSC ion exchange resin bed and precipitated in methanol. The precipitated polymer is dried under vacuum at 80° C. for 24 hours. The resultant polymer was found to have an inherent viscosity of 0.428 dL/g at 25° C. in methylene chloride and a Tg of 261° C.

Film Preparation and Testing Procedure

Two grams of polymer are dissolved in 18 grams of methylene chloride, passed through a course, fritted glass filter onto a clean glass plate and drawn down with a casting blade. The sample is covered until dry, removed from the glass plate and annealed under vacuum at 80° C. for 48 hours. The film has a thickness of 1.16 mils.

From a cast film, a small disc is removed, the mean thickness and standard deviation are determined and the film was then placed in the cell of a fixed volume-variable pressure gas permeability apparatus. Both sides of the membrane are evacuated overnight. One side of the membrane is pressurized with nitrogen at 150 kPaG and the downstream pressure increase is monitored with a pressure transducer and recorded on a single-pen recorder. The pressure gradient across the membrane is 250 kPaA. Gas permeability coefficients are calculated from the slope of the time-pressure curve.

Identical procedures are followed with each gas tested using the following sequence of test gases: nitrogen, methane, nitrogen, oxygen, helium, carbon dioxide. The results are compiled in the Table.

EXAMPLE 2

Polycarbonate Membrane of 100% Tetrachlorobisphenol A

In the apparatus similar to the one described in Example 1 is charged 1,000 cc (2.0 liters) of methylene chloride, 183.2 grams (0.5 moles) of 3,3',5,5' tetrachlorobisphenol A, and 105 cc (1.30 moles) of pyridine. The resultant solution is stirred under a nitrogen atmosphere for 10 minutes. Moderate stirring is continued and 54 grams (0.55 moles) of phosgene is bubbled into the reaction over a 41 minute period.

The solution is then scavenged with methanol, neutralized with dilute hydrochloric acid and washed a second time with dilute hydrochloric acid. The slightly opaque solution is clarified by passing it through an MSC ion exchange resin bed and precipitated in heptane. The precipitated polymer is dried under vacuum at 80° C. for 24 hours. The resultant polymer was found to have an inherent viscosity of 0.72 dL/g at 25° C. in methylene chloride.

A film with a thickness of 1.40 mils is prepared and its permeation characteristics are tested as described in Example 1, the pressure gradient across the membrane is 166 kPaA. The results are compiled in the Table.

EXAMPLE 3

Polycarbonate Membrane of 30% Tetrachlorobisphenol A and 70% Bisphenol A

A film, with a thickness of 2.44 mils, is prepared from a polycarbonate with an inherent viscosity of 0.67, which is a block copolymer derived from 30 percent tetrachlorobisphenol A and 70 percent bisphenol A, and its permeation characteristics are tested as described in Example 1, with a pressure gradient of 350 kPaA across the membrane. The results are compiled in the Table.

EXAMPLE 4

Polycarbonate Membrane of 30% Tetrabromobisphenol A and 70% Bisphenol A

A four-neck, 2.0 liter round bottom flask equipped with a thermometer, air-driven stirrer, and glass funnel is charged with 70.14 grams (0.129 moles) of tetrabromobisphenol A and 1.181 liters of methylene chloride. The mixture is cooled to 5° C. and stirred at 250 rpm's. 25.5 g (0.258 moles) of phosgene is added over eight minutes at about 5° to 6° C. After five minutes, 20.9 milliliters of pyridine is added over a six-minute period, with stirring at 300 rpm's at about 5° to 6° C. The solution is stirred for 30 minutes. Bisphenol A 68.69 g (0.301 moles) is added to the solution. Thereafter, 69.5 milliliters pyridine is added over a five minute period and the temperature went from 1320 to 24° C. Phosgene (17.0 g) is added over a 15-minute period at a temperature of 26° to 27° C. Thereafter, five milliliters of methanol is added. A mixture of HCl and water (490 milliliters and 120 milliliters, respectively) is added over five minutes with stirring at 200 rpm's. Good phase separation is observed. A second wash is performed with a mixture of 15 milliliters HCl and 230 milliliters water.

The polymer is precipitated by adding one volume of polymer solution to four volumes of hexane. The polymer is air dried, then dried in a vacuum oven at about 120° C. The resultant polymer has an inherent viscosity of 0.474 and a Tg of 181° C.

A film, with a thickness of 2.14 mils, is prepared and its permeation characteristics are tested as described in Example 1, the pressure gradient across the membrane is 250 kPaA. The results are compiled in the Table.

EXAMPLE 5

Not an Example of This Invention—Membrane of 100% Bisphenol A

In the apparatus similar to that described in Example 1 (12.0 liters) is charged 7,000 cc of methylene chloride, 961 grams (4.2 moles) of bisphenol A, 12.66 grams of p-tertiary butyl phenol, and 882 cc (10.9 moles) of pyridine. The resultant solution is stirred under a nitrogen atmosphere for 10 minutes. Moderate stirring is continued and 446 grams (4.51 moles) of phosgene is bubbled into the reaction over a 300-minutes period.

The solution is then scavenged with methanol, neutralized with dilute hydrochloric acid and washed a second time with dilute hydrochloric acid. The slightly opaque solution is clarified by passing it through an MSC ion exchange resin bed and precipitated in methanol. The precipitated polymer is dried under vacuum at 80° C. for 24 hours. The resultant polymer was found to have an inherent viscosity of 0.61 dL/g at 25° C. in methylene chloride.

A film, with a thickness of 5.14 mils, is prepared and its permeation characteristics are tested as described in Example 1, with a pressure gradient of 250 kPaA across the membrane. The results are compiled in the Table.

EXAMPLE 6

Polycarbonate Membrane of 100% 3,3',5,5' Tetramethyl Bisphenol A—Not An Embodiment of This Invention In the apparatus as described in Example 1 is charged 500 cc of methylene chloride, 113.7 grams (0.4 moles) of 3,3',5,5'-tetramethyl bisphenol A, and 110 cc (1.36 moles) pyridine. The resultant solution is stirred under a nitrogen atmosphere for 10 minutes. Moderate stirring is continued and 46 grams of (0.46 moles) of phosgene is bubbled into the reaction over a 140-minutes period.

The solution is then scavenged with methanol, neutralized with dilute hydrochloric acid and washed a second time with dilute hydrochloric acid. The slightly opaque solution is clarified by passing it through an MSC ion exchange resin bed and precipitated in methanol. The precipitated polymer is dried under vacuum at 80° C. for 24 hours. The resultant polymer was found to have an inherent viscosity of 0.456 dL/g at 25° C. in methylene chloride.

A film, with a thickness of 2.05 mils, is prepared and its permeation characteristics are tested as described in Example 1, with a pressure gradient across the membrane of 250 kPaA. The results are compiled in the Table.

EXAMPLE 7

Polycarbonate Membrane of 50% 3,3',5,5' Tetramethyl Bisphenol A and 50% Bisphenol A—Not An Example of the Invention A film, with a thickness of 2.50 mils, of a polycarbonate derived from 50 mole percent tetramethyl bisphenol A and 50 mole percent bisphenol A with an inherent viscosity of 0.54 dL/g at 25° C. in methylene chloride is prepared and its permeation characteristics are tested as described in Example 1, with a pressure gradient across the membrane of 252 kPaA. The results are compiled in the Table.

EXAMPLE 8

Polycarbonate Membrane of 30% 3,3',5 5' Tetramethyl Bisphenol A and 70% Bisphenol A—Not An Example of This Invention A film, with a thickness of 1.94 mils, is prepared from a polycarbonate derived from 30 mole percent tetramethyl bisphenol A and 70 mole percent bisphenol A, with an inherent viscosity of 0.81 dL/g at 25° C. in methylene chloride and its permeation characteristics are tested as described in Example 1, with a pressure gradient across the membrane of 254 kPaA. The results are compiled in the Table.

EXAMPLE 9

Polycarbonate Membrane of 70% 3,3',5,5' Tetrachloro Bisphenol A and 30% Bisphenol A In an apparatus similar to the one described in Example 1 (2.0 liters) is charged 1,000 cc of methylene chloride, 117.7 grams (0.35 moles) of 3,3',5,5'-tetrachloro bisphenol A, 34.2 grams (0.15 moles) of bisphenol A, and 105 cc (1.30 moles) of pyridine. The resultant solution is stirred under a nitrogen atmosphere for 10 minutes. Moderate stirring is continued and 54 grams (0.55 moles) of phosgene is bubbled into the reaction over a 70-minute period.

The solution is then scavenged with methanol, neutralized with dilute hydrochloric acid and washed a second time with dilute hydrochloric acid. The slightly opaque solution is clarified by passing it through an MSC ion exchange resin bed and precipitated in methanol. The precipitated polymer is dried under vacuum at 80° C. for 24 hours.

A film, with a thickness of 2.16 mils, is prepared and its permeation characteristics are tested as described in Example 1, with a pressure gradient across the membrane of 250 kPaA. The results are compiled in the Table.

EXAMPLE 10

Polycarbonate Membrane of 70% 3,3',5,5' Tetrabromo Bisphenol A and 30% Bisphenol A In the apparatus similar to the one described in Example 1 (2.0 liters) is charged 1,000 cc of methylene chloride, 190.4 grams (0.35 moles) of 3,3',5,5' tetrabromo bisphenol A, 34.2 grams (0.15 moles) of bisphenol A, and 105 cc (1.30 moles) of pyridine. The resultant solution is stirred under a nitrogen atmosphere for 10 minutes. Moderate stirring is continued and 64 grams (0.65 moles) of phosgene is bubbled into the reaction over a 60-minute period.

The solution is then scavenged with methanol, neutralized with dilute hydrochloric acid and washed a second time with dilute hydrochloric acid. The slightly opaque solution is clarified by passing it through an MSC ion exchange resin bed and precipitated in methanol. The precipitated polymer is dried under vacuum at 80° C. for 24 hours. The resultant polymer was found to have an inherent viscosity of 0.53 dL/g at 25° C. in methylene chloride.

A film, with a thickness of 1.84 mils, is prepared and its permeation characteristics are tested as described in Example 1, with a pressure gradient across the membrane of 250 kPaA. The results are compiled in the Table.

EXAMPLE 11

Polycarbonate Membrane of 15% 3,3',5,5' Tetrabromo Bisphenol A and 85% Bisphenol A—Not An Example of This Invention In an apparatus similar to the one described in Example 1 is charged 1,000 cc of methylene chloride, 40.8 grams (0.75 moles) of 3,3',5,5' tetrabromo bisphenol A, 97.0 grams (0.425 moles) of bisphenol A, and 105 cc (1.30 moles) of pyridine. The resultant solution is stirred under a nitrogen atmosphere for 10 minutes. Moderate stirring is continued and 53 grams (0.54 moles) of phosgene is bubbled into the reaction over a 39-minute period.

The solution is then scavenged with methanol, neutralized with dilute hydrochloric acid and washed a second time with dilute hydrochloric acid. The slightly opaque solution is clarified by passing it through an MSC ion exchange resin bed and precipitated in methanol. The precipitated polymer is dried under vacuum at 80° C. for 24 hours. The resultant polymer was found to have an inherent viscosity of 1.15 dL/g at 25° C. in methylene chloride. A film, with a thickness of 1.36 mils, is prepared and its permeation characteristics are tested as described in Example 1, with a pressure gradient across the membrane of 154 kPaA. The results are compiled in the Table.

EXAMPLE 12

Polycarbonate Membrane of 15% 3,3',5,5' Tetrachloro Bisphenol A and 85% bisphenol A—Not An Example of This Invention In an apparatus similar to the one described in Example 1 (2.0 liters) is charged 1,000 cc of methylene chloride, 25.2 grams (0.75 moles) of 3,3',5,5'-tetrachloro bisphenol A, 9.70 grams (0.425 moles) of bisphenol A, and 105 cc (1.30 moles) of pyridine. The resultant solution is stirred under a nitrogen atmosphere for 10 minutes. Moderate stirring is continued and 55 grams (0.56 moles) of phosgene is bubbled into the reaction over a 44-minute period.

The solution is then scavenged with methanol, neutralized with dilute hydrochloric acid and washed a second time with dilute hydrochloric acid. The slightly opaque solution is clarified by passing it through an MSC ion exchange resin bed and precipitated in methanol. The precipitated polymer is dried under vacuum at 80° C. for 24 hours. The resultant polymer was found to have an inherent viscosity of 0.819 dL/g at 25° C. in methylene chloride.

A film, with a thickness of 2.36 mils, is prepared and its permeation characteristics are tested as described in Example 1, with a pressure gradient across the membrane of 160 kPaA. The results are compiled in the Table.

EXAMPLE 13

Polycarbonate Membrane of 50% 3,3',5,5' Tetrabromo Bisphenol A and 50% Bisphenol A In the apparatus similar as described in Example 1 (2.0 liters) is charged 500 cc of methylene chloride, 54.4 grams (0.10 moles) of 3,3',5,5' tetrabromo bisphenol A, 22.8 grams (0.10 moles) of bisphenol A, and 42 cc (0.52 moles) of pyridine. The resultant solution is stirred under a nitrogen atmosphere for 10 minutes. Moderate stirring is continued and 28 grams (0.28 moles) of phosgene is bubbled into the reaction over a 36-minute period.

The solution is then scavenged with methanol, neutralized with dilute hydrochloric acid and washed a second time with dilute hydrochloric acid. The slightly opaque solution is clarified by passing it through an MSC ion exchange resin bed and precipitated in methanol. The precipitated polymer is dried under vacuum at 80° C. for 24 hours. The resultant polymer was found to have an inherent viscosity of 0.39 dL/g at 25° C. in methylene chloride and a Tg of 203° C.

A film, with a thickness of 3.34 mils, is prepared and its permeation characteristics are tested as described in Example 1, with a pressure gradient across the membrane of 250 kPaA. The results are compiled in the Table.

EXAMPLE 14

Polycarbonate Membrane of 50% 3,3',5,5' Tetrachloro Bisphenol A and 50% Bisphenol A In the apparatus as described in Example 1 is charged 500 cc of methylene chloride, 36.16 grams (0.10 moles) of 3,3',5,5' tetrachloro bisphenol A, 22.8 grams (0.10 moles) of bisphenol A, and 42.0 cc (0.52 moles) of pyridine. The resultant solution is stirred under a nitrogen atmosphere for 10 minutes. Moderate stirring is continued and 28 grams (0.28 Moles) of phosgene is bubbled into the reaction over a 48-minute period.

The solution is then scavenged with methanol, neutralized with dilute hydrochloric acid and washed a second time with dilute hydrochloric acid. The slightly opaque solution is clarified by passing it through an MSC ion exchange resin bed and precipitated in methanol. The precipitated polymer is dried under vacuum at 80° C. for 24 hours. The resultant polymer was found to have an inherent visocsity of 0.51 dL/g at 25° C. in methylene chloride and a Tg of 177° C.

A film, with a thickness of 1.34 mils, is prepared and its permeation characteristics are tested as described in Example 1, with a pressure gradient across the membrane of 250 kPaA. The results are compiled in the Table.

| Ex No. | BISPHENOL | %[1] | P[4] $O_2$ | F[5] $O_2$ | P[4] $N_2$ | F[5] $N_2$ | $O_2/N_2$ | P[4] $CO_2$ | F[5] $CO_2$ | P[4] $CH_4$ | F[5] $CH_4$ | $CO_2/CH_4$ |
|---|---|---|---|---|---|---|---|---|---|---|---|---|
| 1A | TETRABROMO-BISPHENOL A | 100 | .853 | 29.0 | .115 | 3.90 | 7.4 | 3.6 | 122 | .103 | 3.50 | 34.8 |
| 2 | TETRACHLORO-BISPHENOL A | 100 | 1.448 | 40.7 | .231 | 6.50 | 6.3 | 2.6 | 73.2 | .103 | 2.90 | 25.2 |
| 3 | TETRACHLORO-BISPHENOL A | 30 | .8 | 13.3 | .131 | 2.11 | 6.1 | 3.6 | 58.1 | .113 | 1.82 | 31.8 |
| 4 | TETRABROMO-BISPHENOL A | 30 | .8 | 12.9 | .125 | 2.02 | 6.4 | 3.6 | 58.1 | .112 | 1.81 | 32.1 |
| 5[2] | BISPHENOL A[3] | 0 | 1.1 | 8.43 | .208 | 1.59 | 5.3 | 5.5 | 42.2 | .228 | 1.75 | 24.1 |
| 6[2] | TETRAMETHYL-BISPHENOL A | 100 | 3.9 | 73.8 | .78 | 14.8 | 5.0 | 16.3 | 308 | .610 | 11.5 | 26.7 |
| 7[2] | TETRAMETHYL-BISPHENOL A | 50 | 1.4 | 22.0 | .233 | 3.67 | 6.0 | 5.7 | 89.8 | .241 | 3.79 | 23.7 |
| 8[2] | TETRAMETHYL-BISPHENOL A | 30 | 1.3 | 26.4 | .224 | 4.55 | 5.8 | 5.7 | 116 | .206 | 4.18 | 28.8 |
| 9 | TETRACHLORO-BISPHENOL A | 70 | 1.34 | 25.3 | .228 | 4.15 | 6.1 | | | | | |
| 10 | TETRABROMO-BISPHENOL A | 70 | .93 | 19.9 | .14 | 2.99 | 6.7 | | | | | |
| 11[2] | TETRABROMO-BISPHENOL A | 15 | 1.09 | 31.5 | .19 | 5.50 | 5.7 | | | | | |
| 12[2] | TETRACHLORO-BISPHENOL A | 15 | 1.02 | 17.0 | .21 | 3.50 | 4.9 | | | | | |
| 13 | TETRACHLORO-BISPHENOL A | 50 | 1.24 | 14.6 | .23 | 2.71 | 5.4 | 5.49 | 64.7 | .22 | 2.59 | 25 |
| 14 | TETRABROMO-BISPHENOL A | 50 | .98 | 29.3 | .15 | 4.41 | 6.4 | 6.41 | 135 | .16 | 4.70 | 29 |

[1]Remainder is Bisphenol A
[2]Not an embodiment of the invention
[3]Example 5 is a 100% Bisphenol A polycarbonate
[4]P is permeability measured in barrers cc-cm$^2$-s-cm Hg × $10^{-10}$
[5]F is the reduced flux which is calculated by the following formula
F = P ÷ l wherein l is the thickness of the membrane. The units are 1 × $10^{-9}$ cc/cm$^2$ sec cm Hg

EXAMPLE 15

Polycarbonate Membrane of 50% 3,3',5,5'-Tetramethyl Bisphenol A and 50% 3,3',5,5'-Tetrabromo Bisphenol A A three-neck, 1 liter flask equipped with a thermometer, stirrer, and funnel is charged with 54.4 g (0.1 moles) of 3,3',5,5'-tetrabromo bisphenol A, 28.4 g (0.1 moles) of 3,3',5,5'-tetramethyl bisphenol A, 50 cc of pyridine, and 40 cc of methylene chloride. Moderate stirring is initiated and 23 g of phosgene is bubbled into the reactor over a 5½ hour period. The resultant pink turbid solution is then scavenged with methanol, neutralized with dilute HCl and washed a second time with dilute HCl. The slightly hazy solution is clarified by passing it through an MSC resin bed, and precipitated in methanol. The resultant polymer is found to have an inherent viscosity $\eta_{inh}=0.48$ dl/g in methylene chloride.

Two grams of the above sample are dissolved in 18 g of methylene chloride, filtered onto a glass plate and drawn down with a casting blade. The sample is covered until dry, removed from the glass plate and annealed at 80° C. and 760 mm of Hg for forty-eight hours.

From this clear sample, a small disc is removed and is found to have the following permeabilities and selectivities Permeability of $O_2 = 1.87 \times 10^{-10}$ cc-cm/cm$^2$-sec-cm of Hg Permeability of $N_2 = 0.27 \times 10^{-10}$ cc-cm/cm$^2$-sec-cm of Hg $O_2/N_2 = 6.9$ Permeability of $CH_4 = 0.23 \times 10^{-10}$ cc-cm/cm$^2$-sec-cm of Hg Permeability of $CO_2 = 7.01 \times 10^{-10}$ cc-cm/cm$^2$-sec-cm of Hg $CO_2/CH_4 = 30.5$ Permeability of $He = 18.24 \times 10^{-10}$ cc-cm/cm$^2$-sec-cm of Hg Permeability of $CH_4 = 0.24$ cc-cm/cm$^2$-sec-cm of Hg

EXAMPLE 16

Asymmetric Membrane of Tetrabromo Bisphenol A Polycarbonate

A solution of 36 percent tetrabromo bisphenol A polycarbonate in dimethyl formamide (DMF) is poured along one edge of a glass plate. The glass plate is a clean, blemish-free glass plate, whose circumference is framed with masking tape, which is on a level surface. The solution is drawn down to the opposite edge with a 55 mil casting knife. The casting is placed in a warm oven (100° C.) for two minutes. The plate is removed and immersed in a bath of water. The film has an asymmetric structure. After 20 minutes, the opaque film is removed from the bath, separated from the glass plate, patted dry with a paper towel and allowed to air dry for about 16 hours.

A small disc is removed from the air dried film sample. The mean, overall thickness and standard deviation are determined and the film is then placed in the cell of a fixed volume-variable pressure gas permeability apparatus. Both sides of the membrane are evacuated overnight. One side of the membrane is pressurized with nitrogen from 20 to 150 kPaG and the downstream pressure increase is monitored with a pressure transducer and recorded on a single pen recorder. The trans-membrane pressure drop is 120 kPaA for oxygen. Nitrogen is tested at 132 kPaA. A gas permeability coefficient, deviation and flux are determined for oxygen and nitrogen.

The overall thickness of the asymmetric film is about 5.9 mils with a skin thickness of about 0.6 mils. The oxygen permeability is 8.22 barrers with an oxygen flux us $5.0 \times 10^{-6}$ cc/cm$^2$-sec. The reduced flux for oxygen is $5.52 \times 10^{-8}$ cc/cm$^2$-sec-cm Hg. The nitrogen permeability is 1.24 barrers, with a flux of $0.7 \times 10^{-6}$ cc/cm$^2$-sec. The reduced flux for nitrogen is $8.38 \times 10^{-9}$ cc/cm$^2$-sec-cm Hg. The oxygen and nitrogen separation factor is 6.6.

EXAMPLES 17-30

Preferred Spin Conditions for Tetrabromobisphenol A Polycarbonate Hollow Fiber Membranes In order to form a basis from which comparisons can be made, a set of standard spinning and processing conditions are developed. The selection of this standard set of conditions is based on data from early attempts to prepare fibers and corresponds to fiber that is easily formed and gives consistent results from one spin run to another. A series of fourteen experiments using the standard set of conditions are performed to prepare fibers and the fibers are tested for oxygen and nitrogen permeation. The permeation and separation factors for these fourteen experiments are averaged to give a performance standard to measure all other experiments against.

A composition of 52 weight percent tetrabromobisphenol A polycarbonate, 32.5 weight percent N-methyl pyrrolidone (solvent), and 15.5 weight percent of triethylene glycol (non-solvent), (solvent to non-solvent ratio of 2.1 to 1) is fed into the melt pot of a melt pot extruder. Methylene chloride in an amount equal to about 30 weight percent of the total composition is added to the vessel. The mixture is heated to 95° C. and held until the mixture is a homogeneous solution. Most of the methylene chloride flashes during this heating step. A nitrogen purge is passed into the melt pot at 500 cc per minute and nitrogen containing volatilized methylene chloride is withdrawn from a port in the melt pot. From the melt pot the composition is passed to a transfer line and pumped to the spinnerette at a flow rate of 15 g/min. Thirty fibers are spun simultaneously. The transfer line and spinnerette face are held at a temperature of 75° C. The composition is extruded into a hollow fiber shape through an annulus of 254 microns (0.01 inch) with an outside diameter of 1727 microns (0.068 inch) with a core gas pin feeding a core gas of nitrogen down the bore at a rate of 8.8 standard cubic centimeters a minute. The line speed is 100 ft per minute. The fiber is extruded into an air quench zone of a length of 1 foot at ambient temperature. The fiber is passed into a quench bath of water at 4° C. with a residence time of 1.7 seconds. The fiber is taken up and thereafter placed into a bath of water at 90° C. for ten minutes. The fibers are hung vertically and dried by passing air over the fibers at a flow of 100 ft/min over the fibers for about two hours. The fibers prepared have a size of 140×94 microns (OD×ID). All the fibers prepared in these examples and the following examples have a porous outer surface, a porous inner surface, and have a region which separates oxygen from nitrogen as demonstrated by the separation factors stated in each example.

Permeability Testing Procedure

After the fiber is dried, the fibers are tested for permeation properties. The test device is a pressure vessel with four ports, two tubesheet ports, one feed port through which the compressed gas enters the vessel, and an exit or purge port through which the compressed gas can be purged from the vessel. Two hundred ten (210) fibers are passed into one of the tubesheet ports and out the other allowing for a 31.5 cm length of the fibers to be contained within the test device. Epoxy tubesheets are formed in the two tubesheet ports to give a leak-tight bond between the fiber and the two ports. Test units are then pressurized with nitrogen at 50 psig by allowing compressed nitrogen to enter the test device through the feed port while leaving the exit port closed. The exit port is then opened for two minutes to purge the vessel of air and then closed with pure nitrogen left in the vessel. With the exit port closed and the feed port opened, the gas contained within the test device, by means of a pressure driving force, permeates through the walls of the hollow fibers and passes through the lumen of the fibers and out through the tubesheet ports where the flow rate is measured either by means of bubble or mass flow meters. There is negligible back pressure on the gas exiting the tubesheet. After testing with nitrogen, the feed gas is changed to oxygen and the vessel is purged for about two minutes to give pure oxygen at 50 psig in the test device. The amount of oxygen permeating through the fiber walls is measured by combining the outputs from the two tubesheet ports. From these flow measurements, the gas permeation rates and separation factor can be calculated by use of the following equations.

$$\text{Nitrogen flux} = \frac{\text{Measured flow (sccm)}}{\text{surface area of fiber (cm}^2\text{)} \times \text{pressure (cmHg)} \times 60 \text{ seconds/minute)}}$$

$$\text{Oxygen flux} = \frac{\text{Measured flow (sccm)}}{\text{surface area of fiber (cm}^2\text{)} \times \text{pressure (cmHg)} \times 60 \text{ seconds/minute)}}$$

The units are scc/cm$^2$ cmHg sec.
Measured flow = standard cubic centimeters / minute.
Surface area of fibers = 3.14 × OD (outside diameter, cm) × length × the number of fibers.
Pressure (cmHg) = psi × 76 /14.7.
The results are compiled in Table 1.
Separation factor is defined as the Oxygen flux divided by the Nitrogen flux.

TABLE 1

| Example | Oxygen Flux[2] | Oxygen/Nitrogen Separation Factor |
|---|---|---|
| 17 | 4.8 ± .5 | 6.8 ± .1 |
| 18 | 7.4 ± .4 | 6.4 ± .1 |
| 19 | 6.2 ± .1 | 6.4 ± .3 |
| 20 | 7.6 ± .3 | 6.7 ± .1 |
| 21 | 7.0 ± .1 | 5.9 ± .1 |
| 22 | 5.8 ± .2 | 6.8 ± .2 |
| 23 | 9.0 ± .2 | 6.8 ± .2 |
| 24 | 8.3 ± .1 | 6.7 ± .1 |
| 25 | 7.2 ± .1 | 6.0 ± .2 |
| 26[1] | 4.4 ± .4 | 6.0 ± .2 |
| 27 | 6.5 ± .3 | 6.0 ± .5 |
| 28 | 6.1 ± .1 | 6.2 ± .1 |
| 29 | 7.4 ± .1 | 6.5 ± .1 |
| 30 | 8.1 ± .1 | 6.6 ± .2 |
| AVERAGE | 7.0 ± 1.1 | 6.4 ± .3 |

[1]Not included in average, suspect blend composition
[2]Units (1 × 10$^{-6}$) scc/cm$^2$ · cm Hg · sec

What is claimed is:

1. A semi-permeable gas separation membrane comprising a thin discriminating layer consisting predominantly of a carbonate polymer derived from a bisphenol corresponding to formula I

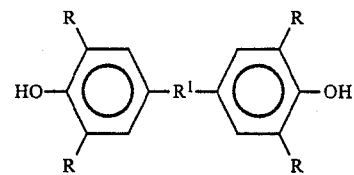

where R at each occurrence is independently H, Cl, Br, or C$_1$-C$_4$ alkyl and R$^1$ is

—S—, —SO$_2$—, —O—, or a C$_1$-C$_6$ divalent hydrocarbon a C$_1$-C$_6$ divalent fluorocarbon radical or inertly substituted hydrocarbon radical, with the proviso that at least 25 weight percent of the moieties derived from the bisphenol of Formula I present in the discriminating layer bear R groups which are exclusively Br or Cl, said gas separation membrane exhibiting a separation factor for oxygen and nitrogen at 24° C. of at least 6.1 and a reduced flux of 3.35×10$^{-9}$ cc/cm$^2$-sec-cm Hg or greater for oxygen.

2. The membrane of claim 1 wherein at least 35 weight percent of the moieties derived from the bisphenol of Formula I present in the discriminating layer bear R groups with which are exclusively Br or Cl.

3. The membrane of claim 2 wherein at least 50 weight percent of the moieties derived from the bisphenol of Formula I present in the discriminating layer bear R groups which are exclusively Br or Cl.

4. The membrane of claim 3 wherein R$^1$ is a C$_1$-6 divalent hydrocarbon radical.

5. The membrane of claim 4 wherein the remainder of the moieties derived from the bisphenol of Formula I present in the discriminating layer bear R groups which are exclusively C$_{1-4}$ alkyl.

6. The membrane of claim 3 wherein the thin discriminating layer consists predominantly of a carbonate polymer derived from between about 50 and 100 percent of a bisphenol of Formula III

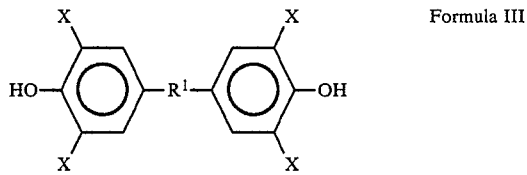

Formula III and 0 and 50 percent of a bisphenol of Formula IV

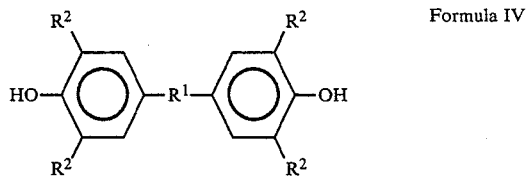

Formula IV where
R$^1$ is a C$_{1-6}$ divalent hydrocarbon;
R$^2$ is C$_{1-4}$ alkyl; and
X is chlorine or bromine.

7. The membrane of claim 6 wherein R$^2$ is methyl.

8. The membrane of claim 3 wherein 100 weight percent of the moieties derived from Formula I present in the discriminating layer bear R groups which are exclusively Br or Cl.

9. The membrane of claim 8 wherein at least 50 weight percent of the moieties derived from Formula I present in the discriminating layer bear R groups which are exclusively Br.

10. The membrane of claim 2 wherein at least 35 weight percent of the moieties derived from Formula I present in the descriminating layer bear R groups which are exclusively Br, said gas separation membrane exhibiting a separation factor for oxygen and nitrogen at 20° C. of at least 6.4 and a reduced flux of $1.12 \times 10^{-8}$ cc/cm$^2$-sec-cm Hg or greater for oxygen.

11. The membrane of claim 10 wherein at least 50 weight percent of the moieties derived from Formula I bear R groups which are exclusively Br.

12. The membrane of claim 11 wherein the remainder of the R groups are $C_{1-4}$ alkyl, and $R^1$ is a $C_{1-6}$ divalent hydrocarbon.

13. The membrane of claim 12 wherein the remainder of the R groups are methyl and $R^1$ is a $C_{1-6}$ alkylidine moiety.

14. The membrane of claim 11 wherein 100 weight percent of the moieties derived from Formula I bear R groups which are exclusively bromine.

15. The membrane of claim 14 wherein $R^1$ is a $C_{1-6}$ divalent hydrocarbon.

16. The membrane of claim 15 wherein the bisphenol is tetrabromobisphenol A and the said gas separation membrane has a separation factor of at least 7.0 at 20° C.

17. A process for separating oxygen from nitrogen which comprises contacting a gaseous stream containing oxygen and nitrogen with the membrane of claim 1 under conditions such that oxygen selectively permeates through the membrane, in comparison to nitrogen.

18. The process of claim 17 wherein the membrane is sealingly engaged to a vessel which defines a space communicating with only one side of the membrane, such that the permeable oxygen contacting the other side of the membrane can permeate through the membrane to the non-communicating space.

19. The process of claim 18 which comprises
a. contacting the gas stream, with the membrane under conditions such that oxygen selectively permeates through the membrane to the other side of the membrane;
b. removing the permeated oxygen from the vicinity of the membrane; and
c. removing the unpermeated nitrogen from the vicinity of the membrane.

20. The process of claim 19 wherein the membrane has a separation factor of 6.7 or greater at 20° C.

21. The process of claim 19 wherein the remainder of the R groups are hydrogen or methyl and $R^1$ is a $C_{1-6}$ divalent hydrocarbon.

22. The process of claim 21 wherein 100 weight percent of the moieties derived from Formula I bear R groups which are exclusively bromine.

23. The process of claim 22 wherein $R^1$ is a $C_{1-6}$ alkylidene moiety.

24. The process of claim 23 wherein the bisphenol is tetrabromo bisphenol A.

25. A semi-permeable asymmetric gas separation membrane comprising a thin discriminating layer consisting predominantly of a carbonate polymer derived from a bisphenol corresponding to Formula I

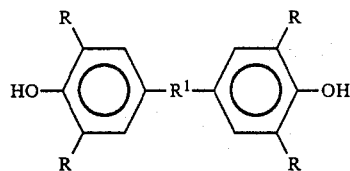

where R at each occurrence is independently H, Cl, Br, or $C_1$-$C_4$ alkyl and $R^1$ is

—S—, —SO$_2$—, —O—, or a $C_1$-$C_6$ divalent hydrocarbon a $C_1$-$C_6$ divalent fluorocarbon radical or inertly substituted hydrocarbon radical, with the proviso that at least 25 weight percent of the moieties derived from the bisphenol of Formula I present in the discriminating layer bear R groups which are exclusively Br or Cl, said gas separation membrane exhibiting a separation factor for oxygen and nitrogen at 24° C. of at least 6.1 and a reduced flux of $8.53 \times 10^{-8}$ cc/cm$^2$-sec-cm Hg or greater for oxygen.

26. The membrane of claim 25 wherein at least 35 weight percent of the moieties derived from the bisphenol of Formula I present in the discriminating layer bear R groups with which are exclusively Br or Cl.

27. The membrane of claim 26 wherein at least 50 weight percent of the moieties derived from the bisphenol of Formula I present in the discriminating layer bear R groups which are exclusively Br or Cl.

28. The membrane of claim 27 wherein $R^1$ is a $C_{1-6}$ divalent hydrocarbon radical.

29. The membrane of claim 28 wherein the remainder of the moieties derived from the bisphenol of Formula I present in the discriminating layer bear R groups which are exclusively $C_{1-4}$ alkyl.

30. The membrane of claim 27 wherein 100 weight percent of the moieties derived from Formula I present in the discriminating layer bear R groups which are exclusively Br or Cl.

31. The membrane of claim 30 wherein at least 50 weight percent of the moieties derived from Formula I present in the discriminating layer bear R groups which are exclusively Br.

32. The membrane of claim 26 wherein at least 35 weight percent of the moieties derived from Formula I present in the descriminating layer bear R groups which are exclusively Br, said gas separation membrane exhibiting a separation factor for oxygen and nitrogen at 20° C. of at least 6.4 and a reduced flux of $5.69 \times 10^{-6}$ cc/cm$^2$-sec-cm Hg or greater for oxygen.

33. The membrane of claim 32 wherein at least 50 weight percent of the moieties derived from Formula I bear R groups which are exclusively Br.

34. The membrane of claim 33 wherein the remainder of the R groups are $C_{1-4}$ alkyl, and $R^1$ is a $C_{1-6}$ divalent hydrocarbon.

35. The membrane of claim 34 wherein the remainder of the R groups are methyl and $R^1$ is a $C_{1-6}$ alkylidine moiety.

36. The membrane of claim 35 wherein 100 weight percent of the moieties derived from Formula I bear R groups which are exclusively bromine.

37. The membrane of claim 36 wherein $R^1$ is a $C_{1-6}$ divalent hydrocarbon.

38. The membrane of claim 37 wherein the bisphenol is tetrabromobisphenol A and the said gas separation membrane has a separation factor of at least 7.0 at 20° C.

39. A process for separating oxygen from nitrogen which comprises contacting a gaseous stream containing oxygen and nitrogen with the membrane of claim 25 under conditions such that oxygen selectively permeate through the membrane, in comparison to nitrogen.

40. The process of claim 39 wherein the membrane is sealingly engaged to a vessel which defines a space communicating with only one side of the membrane, such that the permeable oxygen contacting the other side of the membrane can permeate through the membrane to the non-communicating space.

41. An asymmetric gas separation membrane comprising a thin, discriminating layer consisting predominantly of a carbonate polymer derived from a bisphenol corresponding to Formula I

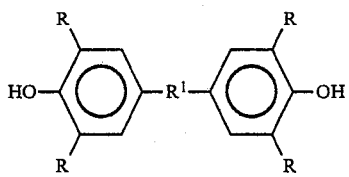

wherein R at each occurrence is independently H, C, Br, or $C_1$–$C_4$ alkyl and $R^1$ is

—S—, —$SO_2$—, —O—, or a $C_1$–$C_6$ divalent hydrocarbon a $C_1$–$C_6$ divalent fluorocarbon radical or inertly substituted hydrocarbon radical, with the proviso that at least 25 weight percent of the moieties derived from the bisphenol of Formula I present in the discriminating layer bear R groups which are exclusively Br or Cl, said gas separation membrane exhibiting a separation factor for oxygen and nitrogen at 25° C. of at least 6.1 and a flux of $1.77 \times 10^{-5}$ cc/cm$^2$-sec for oxygen.

42. The membrane of claim 41 wherein at least 50 weight percent of the moieties derived from the bisphenol of Formula I present in the discriminating layer bear R groups which are exclusively Br or Cl.

43. The membrane of claim 42 wherein $R^1$ is a $C_{1-6}$ divalent hydrocarbon radical.

44. The membrane of claim 42 wherein 100 weight percent of the moieties derived from Formula I present in the discriminating layer bear R groups which are exclusively Br or Cl.

45. The membrane of claim 41 wherein at least 35 weight percent of the moieties derived from Formula I present in the descriminating layer bear R groups which are exclusively Br, said gas separation membrane exhibiting a separation factor for oxygen and nitrogen at 20° C. of at least 6.5 and a flux of $1.15 \times 10^{-3}$ cc/cm$^2$-sec or greater for oxygen.

46. The membrane of claim 45 wherein at least 50 weight percent of the moieties derived from Formula I bear R groups which are exclusively Br.

47. The membrane of claim 46 wherein 100 weight percent of the moieties derived from Formula I bear R groups which are exclusively bromine.

48. The membrane of claim 47 wherein $R^1$ is a $C_{1-6}$ divalent hydrocarbon.

49. The membrane of claim 48 wherein the bisphenol is tetrabromobisphenol A and the said gas separation membrane has a separation factor of at least 7.0 at 20° C. with a flux of $3.52 \times 10^{-3}$ cc/cm$^2$-sec or greater.

50. A process for separating oxygen from nitrogen which comprises contacting a gaseous stream containing oxygen and nitrogen with the membrane of claim 41 under conditions such that oxygen selectively permeates through the membrane, in comparison to nitrogen.

51. The process of claim 50 wherein the membrane is sealingly engaged to a vessel which defines a space communicating with only one side of the membrane, such that the permeable oxygen contacting the other side of the membrane can permeate through the membrane to the non-communicating space.

52. A composite gas separation membrane comprising a porous support and a thin, discriminating layer consisting predominantly of a carbonate polymer derived from a bisphenol corresponding to Formula I

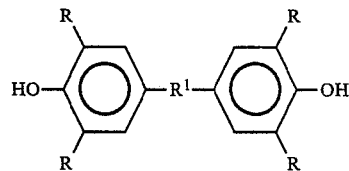

wherein R at each occurrence is independently H, Cl, Br, or $C_1$–$C_4$ alkyl and $R^1$ is

—S—, —$SO_2$—, —O—, or a $C_1$–$C_6$ divalent hydrocarbon or a $C_1$–$C_6$ divalent fluorocarbon radical or inertly substituted hydrocarbon radical, with the proviso that at least 25 weight percent of the moieties derived from the bisphenol of Formula I present in the discriminating layer bear R groups which are exclusively Br or Cl, said gas separation membrane exhibiting a separation factor for oxygen and nitrogen at 24° C. of at least 6.1 and a flux of $1.77 \times 10^{-5}$ cc/cm$^2$-sec for oxygen.

53. The membrane of claim 52 wherein 100 weight percent of the moieties derived from Formula I present in the discriminating layer bear R groups which are exclusively Br or Cl.

54. The membrane of claim 53 wherein at least 50 weight percent of the moieties derived from Formula I present in the discriminating layer bear R groups which are exclusively Br, said gas separation membrane exhibiting a separation factor for oxygen and nitrogen at 20° C. of at least 6.4 and a flux of $1.15 \times 10^{-3}$ cc/cm$^2$-sec barrers or greater for oxygen.

55. The membrane of claim 54 wherein 100 weight percent of the moieties derived from Formula I bear R groups which are exclusively bromine.

56. The membrane of claim 55 wherein $R^1$ is a $C_{1-6}$ divalent hydrocarbon.

57. The membrane of claim 56 wherein the bisphenol is tetrabromobisphenol A and the said gas separation membrane has a separation factor of at least 7.0 at 20° C. with a flux of $3.52 \times 10^{-3}$ cc/cm$^2$-sec barrers or greater.

58. A process for separating oxygen from nitrogen which comprises contacting a gaseous stream containing oxygen and nitrogen with the membrane of claim 52 under conditions such that oxygen selectively permeates through the membrane, in comparison to nitrogen.

59. The process of claim 58 wherein the membrane is sealingly engaged to a vessel which defines a space communicating with only one side of the membrane, such that the permeable oxygen contacting the other side of the membrane can permeate through the membrane to the non-communicating space.

* * * * *

UNITED STATES PATENT AND TRADEMARK OFFICE
CERTIFICATE OF CORRECTION

PATENT NO.  : 4,818,254

DATED       : April 4, 1989

INVENTOR(S) : Joginder N. Anand, Darrell C. Feay, Stephen E. Bales, Thomas O. Jeanes It is certified that error appears in the above-identified patent and that said Letters Patent is hereby corrected as shown below:

Col. 2, line 18, delete "where" and insert -- wherein --;

Col. 3, line 66, after "Preferably" insert a comma;

Col. 4, lines 17-26, change formula as follows:

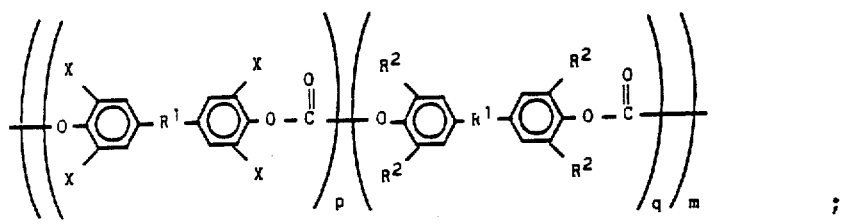

Col. 4, line 56, before "reference" delete "be" and insert -- by --;

Col. 5, line 23, "pyrrolidinone" has been misspelled;

Col. 6, line 25, after "of" insert -- a --;

Col. 6, line 59, "requires" has been misspelled;

Col. 6, line 66, delete "0.2∞" and insert -- 0.2µ --;

UNITED STATES PATENT AND TRADEMARK OFFICE
CERTIFICATE OF CORRECTION

PATENT NO. : 4,818,254

DATED : April 4, 1989

INVENTOR(S) : Joginder N. Anand, Darrell C. Feay, Stephen E. Bales, Thomas O. Jeanes It is certified that error appears in the above-identified patent and that said Letters Patent is hereby corrected as shown below:

Col. 8, line 34, delete "SPECIFIED" and insert -- SPECIFIC --;

Col. 8, line 54, delete "minutes" and insert -- minute --;

Col. 10, line 5, delete "1320" and insert -- 13 --;

Col. 10, line 35, delete "minutes" and insert -- minute --;

Col. 10, line 61, delete "minutes" and insert -- minute --;

Col. 12, line 27, delete "0.75" and insert -- 0.075 --;

Col. 14, line 20, "viscosity" has been misspelled;

Col. 14, line 4 of the footnote under the table, delete "$cc-cm^2-s-cm\ Hg$" and insert -- ($cc-cm/cm^2-s-cm\ Hg$) --;

Col. 14, line 14 of the table, delete "6.41" and insert -- 4.61 --;

Col. 14, line 67, delete "40" and insert -- 400 --;

Col. 15, line 51, "evacuated" has been misspelled;

Col. 15, line 63, delete "us" and insert -- is --;

Col. 18, line 10, delete "where" and insert -- wherein --;

Col. 18, line 64, delete "where" and insert -- wherein --;

UNITED STATES PATENT AND TRADEMARK OFFICE
CERTIFICATE OF CORRECTION

PATENT NO. : 4,818,254

DATED : April 4, 1989

INVENTOR(S) : Joginder N. Anand, Darrell C. Feay, Stephen E. Bales, Thomas O. Jeanes It is certified that error appears in the above-identified patent and that said Letters Patent is hereby corrected as shown below:

Col. 19, line 11, "discriminating" has been misspelled;

Col. 20, line 10, delete "where" and insert -- wherein --;

Col. 20, line 51, "discriminating" has been misspelled;

Col. 21, line 9, delete "permeate" and insert -- permeates --;

Col. 21, line 30, delete "C" and insert -- Cl --;

Col. 21, line 44, delete "25°C" and insert -- 24°C --;

Col. 21, line 58, "discriminating" has been misspelled;

Col. 21, line 61, delete "6.5" and insert -- 6.4 --.

Signed and Sealed this

Third Day of March, 1992

Attest:

HARRY F. MANBECK, JR.

Attesting Officer

Commissioner of Patents and Trademarks